US 8,357,519 B2

(12) United States Patent
Yang

(10) Patent No.: US 8,357,519 B2
(45) Date of Patent: Jan. 22, 2013

(54) METHODS AND PROCESSES FOR PRODUCING ESTERS

(75) Inventor: Shang-Tian Yang, Dublin, OH (US)

(73) Assignee: The Ohio State University, Columbus, OH (US)

(*) Notice: Subject to any disclaimer, the term of this patent is extended or adjusted under 35 U.S.C. 154(b) by 520 days.

(21) Appl. No.: 12/621,982

(22) Filed: Nov. 19, 2009

(65) Prior Publication Data

US 2010/0124773 A1 May 20, 2010

Related U.S. Application Data

(60) Provisional application No. 61/116,108, filed on Nov. 19, 2008.

(51) Int. Cl.
C12P 7/62 (2006.01)
C12P 7/40 (2006.01)
B01D 11/04 (2006.01)
C12N 1/20 (2006.01)
C12M 1/00 (2006.01)

(52) U.S. Cl. ............... 435/135; 435/136; 435/252.7; 435/297.4; 210/634

(58) Field of Classification Search ............... 435/135, 435/136, 252.7, 297.4; 210/634
See application file for complete search history.

(56) References Cited

U.S. PATENT DOCUMENTS

| 3,478,112 A | 11/1969 | Adam et al. |
| 4,110,165 A * | 8/1978 | Cole et al. ............ 435/119 |
| 4,443,639 A | 4/1984 | Pesa et al. |
| 5,132,217 A | 7/1992 | Gabelman |
| 5,563,069 A | 10/1996 | Yang |
| 5,753,474 A | 5/1998 | Ramey |
| 6,204,417 B1 | 3/2001 | Fischer et al. |
| 6,927,048 B2 | 8/2005 | Verser et al. |
| 2009/0297482 A1* | 12/2009 | Dicks et al. ............ 424/93.4 |
| 2010/0159553 A1 | 6/2010 | Bradin |

OTHER PUBLICATIONS

Wu et al., "Extractive fermentation for butyric acid production from glucose by *Clostridium tyrobutyricum*," Biotechnology and Bioengineering 82(1):93-102, 2003.*
Santos et al., "Optimization of lipase-catalysed synthesis of butyl butyrate using a factorial design", World Journal of Microbiology & Biotechnology (2006) 22:1007-1011.
Brekke, "Butanol an Energy Alternative?", EthanolToday, Mar. 2007, pp. 36-39.
Ramey et al., "Production of Butyric Acid and Butanol from Biomass", Final Report, 2004, pp. 1-103.
Wu et al., "Extractive Fermentation for Butyric Acid Production From Glucose by *Clostridium tyrobutyricum*", Biotechnology and Bioengineering, vol. 82, No. 1, Apr. 5, 2003, pp. 93-102.
Zhu et al., "Butyric acid production from acid hydrolysate of corn fibre by *Clostridium tyrobutyricum* in a fibrous-bed bioreactor", Process Biochemistry, 38 (2002), pp. 657-666.

(Continued)

*Primary Examiner* — Rosanne Kosson
(74) *Attorney, Agent, or Firm* — Dinsmore & Shohl LLP

(57) ABSTRACT

Methods are provided for producing esters. The methods comprise converting a fermentable carbon source to organic acids by fermentation with organic acid producing microorganisms, followed by catalytic esterification. The methods comprise integrated fermentation, extraction, and esterification reactions wherein the organic acids produced during fermentation are extracted into an extraction solvent and then directly reacted with an alcohol in the presence of a catalyst to form organic esters. Methods of producing esters are also provided wherein the organic acids produced during fermentation and extracted into the extraction solvent are stripped from the extraction solvent prior to being reacted with an alcohol in the presence of a catalyst to form organic esters.

23 Claims, 10 Drawing Sheets

OTHER PUBLICATIONS

Liu et al., "Construction and Characterization of ack Deleted Mutant of *Clostridium tyrobutyricum* for Enhanced Butyric Acid and Hydrogen Production", Biotechnology Prog., 2006, 22, pp. 1265-1275.

Zhu et al., "Construction and Characterization of pta Gene-Deleted Mutant of *Clostridium tyrobutyricum* for Enhanced Butyric Acid Fermentation", Biotechnology and Bioengineering, vol. 90, No. 2, Apr. 20, 2005, pp. 154-166.

Liu et al., "Butyric acid and hydrogen production by *Clostridium tyrobutyricum* ATCC 25755 and mutants", Enzyme and Microbial Technology, 38 (2006), pp. 521-528.

Liu et al., "Kinetics of butyric acid fermentation of glucose and xylose by *Clostridium tyrobutyricum* wild type and mutant", Process Biochemistry, 41 (2006), pp. 801-808.

* cited by examiner

METHODS AND PROCESSES FOR PRODUCING ESTERS

CROSS REFERENCE TO RELATED APPLICATIONS

This application claims priority to U.S. Provisional Application Ser. No. 61/116,108, filed Nov. 19, 2008, the contents of which are hereby incorporated by reference in its entirety.

TECHNICAL FIELD

The present invention is generally directed to methods and processes for producing organic acid esters, and more specifically to methods of producing organic acid esters via fermentation, extraction, and enzymatic esterification in an integrated process to reduce process steps and production costs.

BACKGROUND

The conversion of organic acids and alcohols to corresponding organic esters for industrial applications has been widely studied. Organic esters are used in a wide variety of applications, including the areas of biofuels, food flavors and fragrances, and solvents.

Fermentation processes using microorganisms provide a promising path for converting biomass and agricultural wastes into chemicals and fuels. There are abundant low-value agricultural commodities and food processing byproducts or wastes that require proper disposal to avoid pollution problems. In the dairy industry, approximately 80 billion pounds of cheese whey byproduct are generated annually, much of which has no economical use and requires costly disposal. Similarly, in the corn refinery industry, more than 22% of the estimated 12 billion bushels (approximately 300 million metric tons) of corn annually produced in the United States is processed to produce high-fructose-corn-syrup, dextrose, starch, and fuel alcohol. It is thus desirable to convert these byproducts and wastes to high-value products to reduce waste while improving the process economics.

Bioethanol is the major biofuel currently available on the market. Recently, however, biobutanol has attracted attention for its potential as a transportation fuel because biobutanol is noncorrosive and offers a safer fuel that can be dispersed through existing pipelines and filling stations. As a biofuel, butanol has the following advantages over ethanol: (a) butanol has 30% more Btu per gallon; (b) butanol is less evaporative/explosive with a Reid vapor pressure (RVP) 7.5 times lower than ethanol; (c) butanol is safer than ethanol because of its higher flash point and lower vapor pressure; and (d) butanol is more miscible with gasoline and diesel fuel but less miscible with water.

Butyrate esters have similar energy content and properties to biobutanol but offer the advantage of being easier to produce than biobutanol. More specifically, butyrate esters have similar energy content to butanol, are substantially insoluble in water, and have lower vapor pressures and higher flash points than ethanol. Butyrate esters may be produced from sugars via butyric acid fermentation followed by esterification with an alcohol. Thus, butyrate esters offer a novel alternative to existing biofuels.

Short-chain organic acid esters are also widely used as flavor and fragrance compounds in food, beverage, cosmetic, and pharmaceutical industries. Currently, most of the flavor compounds are provided by traditional methods such as chemical synthesis or extraction from natural sources. As a result, additional embodiments for methods and processes for producing esters are desired.

SUMMARY

The present invention relates generally to methods for producing esters. According to one embodiment of the present invention, the methods comprise converting a fermentable carbon source to organic acids by fermentation with organic acid producing microorganisms, followed by catalytic esterification. In a further embodiment of the present invention, the methods comprise integrated fermentation, extraction, and esterification reactions wherein the organic acids produced during fermentation are extracted into an extraction solvent and then directly reacted with an alcohol in the presence of a catalyst to form organic esters. The organic esters are then stripped from the extraction solvent with steam in a distillation column. The extraction solvent is thus regenerated and recycled for the extraction process, while the ester and unreacted alcohol will be separated in the distillation process.

In an alternative embodiment of the present invention, methods for producing esters are provided wherein the organic acids produced during fermentation and extracted into an extraction solvent are stripped from the extraction solvent prior to being reacted with an alcohol in the presence of a catalyst to form organic esters.

These and other features and advantages of these and other various embodiments according to the present invention will become more apparent in view of the drawings, detailed description, and claims provided that follow hereafter.

BRIEF DESCRIPTION OF THE DRAWINGS

The following detailed description of the embodiments of the present invention can be best understood when read in conjunction with the following drawings, where like structure is indicated with like reference numerals, and in which.

Figure 8:
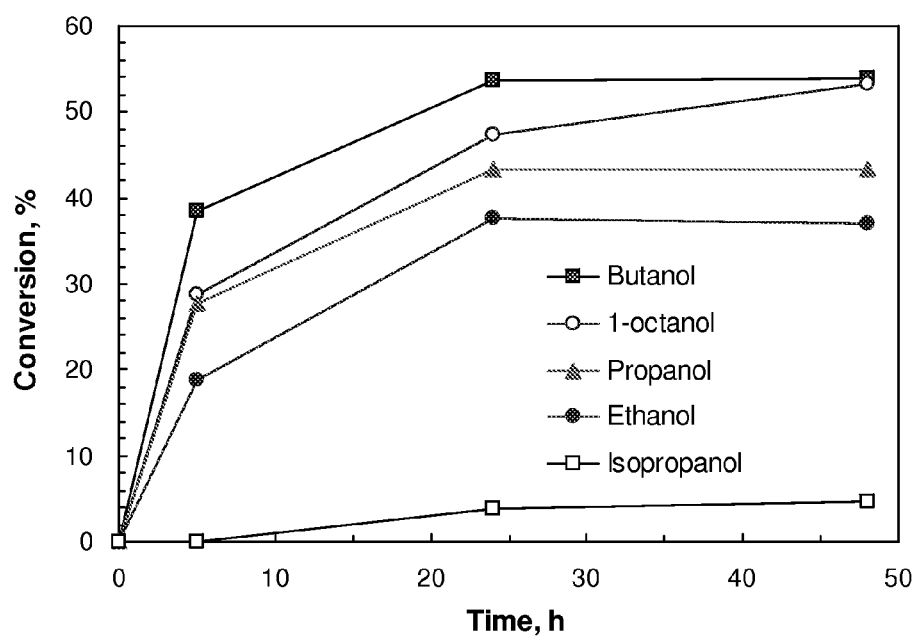

FIG. 8 shows the kinetics of lactic acid ester synthesis with lactic acid and various alcohols under the reaction conditions: 0.9 g immobilized *Candida* sp. 99-125 lipase, 0.5 ml of 85% (w/w) lactic acid (30 g/l), 2.8 M alcohol, 1.5 ml of Alamine 336 and 2-octanol with a total volume of 10 ml at 30° C. and 150 rpm.

Figure 9:
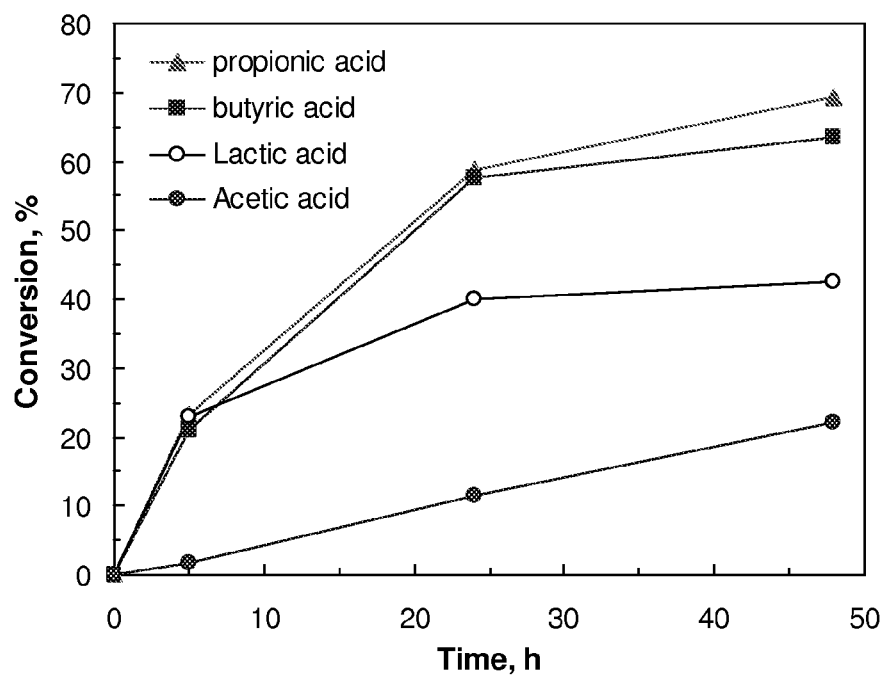

FIG. 9 shows the kinetics of ethyl ester synthesis with ethanol and various organic acids under the reaction conditions: 0.9 g immobilized *Candida* sp. 99-125 lipase, 0.33 M acid, 1.6 ml of ethanol, 1.5 ml of Alamine 336 and 2-octanol with a total volume of 10 ml at 30° C. and 150 rpm.

Figure 10:
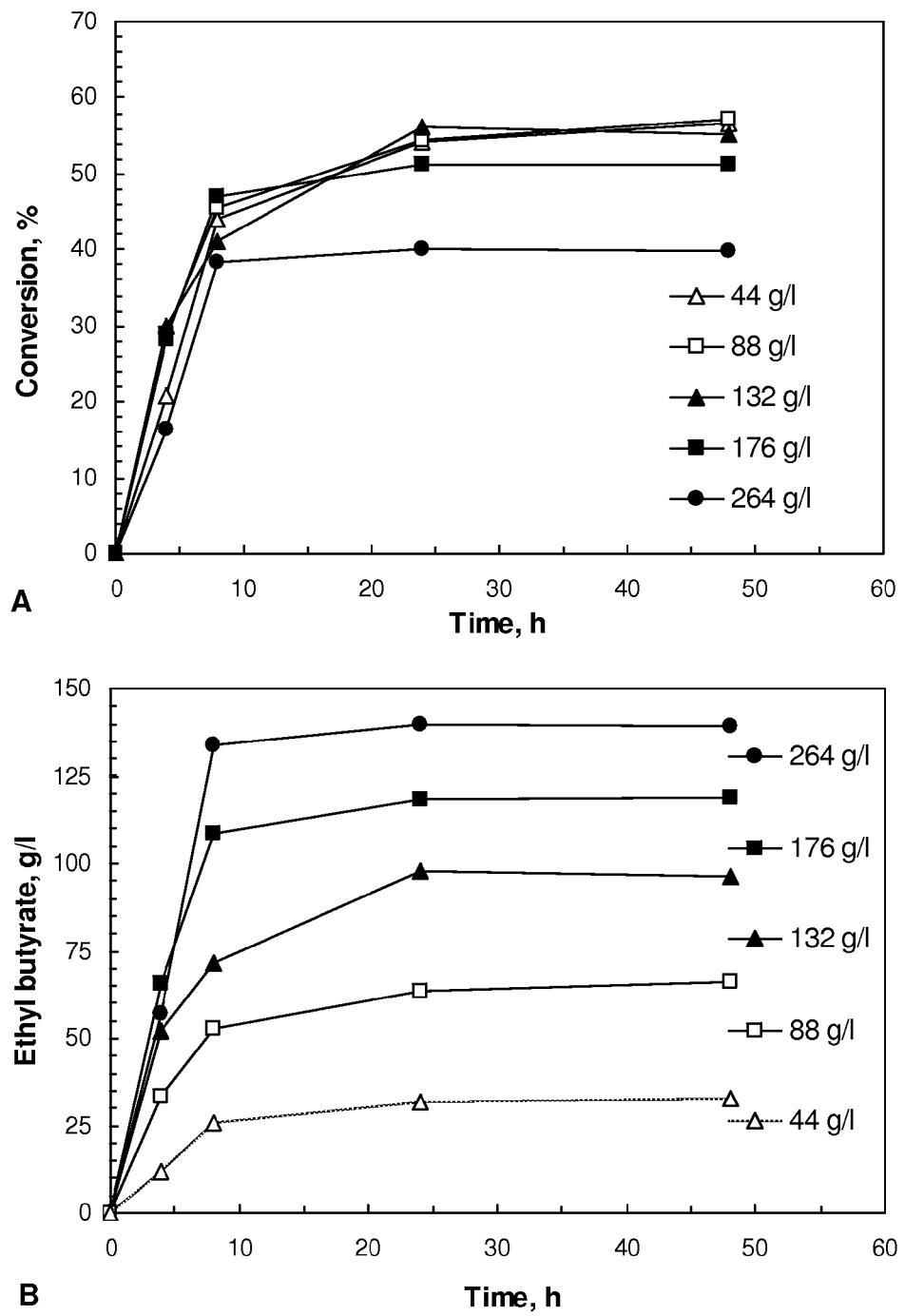

FIG. 10 shows two graphs illustrating the kinetics of the biosynthesis of ethyl butyrate with ethanol and butyric acid with the butyric acid at various concentrations under the following reaction conditions: 0.9 g immobilized *Candida* sp. 99-125 lipase, 2.3 ml of ethanol, 1.5 ml of Alamine 336 and 2-octanol with a total volume of 10 ml at 30° C. and 150 rpm.

DETAILED DESCRIPTION

The present invention comprises methods and processes for producing esters. The methods and processes comprise converting a fermentable carbon source to organic acids by fermentation with organic acid producing microorganisms, followed by catalytic esterification. The methods and processes of the present invention comprise integrated fermentation, extraction, and esterification reactions wherein the organic acids produced during fermentation are extracted into an extraction solvent and then directly reacted with an alcohol in the presence of a catalyst to form organic esters. The present invention also relates to methods and processes of producing esters wherein the organic acids produced during fermentation and extracted into the extraction solvent are stripped from the extraction solvent prior to being reacted with an alcohol in the presence of a catalyst to form organic esters.

Figure 1:
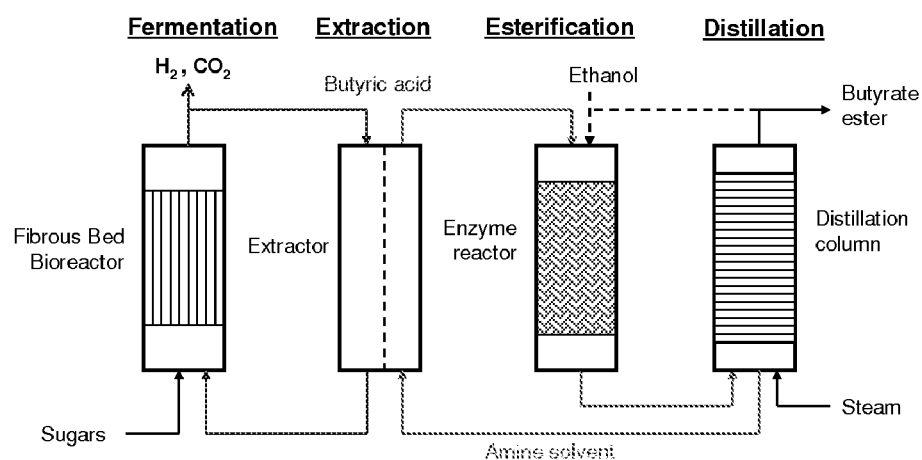
FIG. 1 is a flow chart illustrating one embodiment of the integrated fermentation-extraction-esterification process for the production of butyrate esters.

In one embodiment of the present invention, as depicted in FIG. 1, the fermentation, extraction, and esterification reactions are integrated. In accordance with this particular embodiment of the present invention, the fermentation process is carried out by converting a fermentable carbon source to organic acids by fermentation with microorganisms, wherein the fermentable carbon source is derived from biomass feedstocks. Suitable sources of fermentable carbon sources include any sources of carbon that may be used in the fermentation process to produce organic acids. In one specific embodiment, the fermentable carbon source may include but is not limited to sugars, starch, cellulose and glycerol. In another specific embodiment, the carbon source may comprise a carbohydrate source. In yet still a further embodiment, the carbon source may be derived from biomass feedstocks. Suitable sources of biomass feedstocks include agricultural residues such as corn stovers, corn cobs, and rice straw, and processing wastes such as cheese whey and corn fiber. After sterilization by microfiltration, cheese whey, which contains mainly lactose, can be hydrolyzed with lactase immobilized in a fibrous bed reactor, facilitating organic acid fermentation by organic acid producing microorganisms. Suitable microorganisms include but are not limited to bacteria, yeasts, and filamentous fungi. The main byproducts from the corn milling process are corn fibers and steep liquor, which must be properly converted to marketable products in order to avoid the high waste treatment costs due to the high biological oxygen demand (BOD) content. In addition to sugars (starch, glucose, fructose, etc.) present in these processing wastes, there are also abundant sugars (glucose and xylose) present in cellulose and hemicellulose found in corn stovers, corn cobs, rice straw and many other agricultural residues and plant biomass. Corn fiber can be hydrolyzed with dilute HCl to yield glucose and xylose, both of which can be readily fermented by organic acid producing microorganisms.

In one embodiment of the present invention, the fermentation process is carried out by feeding a fermentable carbon source derived from feedstock into a bioreactor, such as a fibrous bed bioreactor as disclosed in U.S. Pat. No. 5,563,069. Conversion of the fermentable carbohydrates to organic acids is accomplished via fermentation by organic-acid producing microorganisms. Additionally, in one embodiment of the present invention, the fermentation process is conducted at a pH from approximately 4 to 7.

In one specific embodiment, butyric acid fermentation by butyric acid producing bacteria is carried out in a fibrous bed bioreactor. Several species of bacteria can produce butyric acid as the major fermentation product from a wide range of substrates. Among them, *Clostridium tyrobutyricum* possesses several advantages over other species of bacteria, including high product purity, high product yield, and simple medium for cell growth. However, the fermentation reaction may also utilize other butyric acid producing microorganisms such as: *Clostridium butyricum*, *Clostridium beijerinckii*, *Clostridium populeti*, and *Clostridium thermobutyricum*, as the specific recitation of *Clostridium tyrobutyricum* is not meant to limit the scope of the invention.

However, like other acidogenic bacteria, butyric acid bacteria are strongly inhibited by their acid products. Thus, in response to these difficulties, a butyric acid fermentation process has been developed wherein engineered mutants of *Clostridium tyrobutyricum* ATCC 25755 are obtained from inactivating the chromosomal ack gene encoding acetate kinase, and adapting into a fibrous bed bioreactor. The *Clostridium tyrobutyricum* ATCC 25755 are preferably used in fermentation reactions to produce butyric acid. The *Clostridium tyrobutyricum* mutants with the inactive chromosomal ack gene show high butyric acid yield of up to 48% (w/w), final butyric acid concentration of up to 80 g/L, and high productivity (>2 g/L·h) of butyric acid from glucose.

In an alternative embodiment of the present invention, propionic acid fermentation has also been developed for propionic acid using the propionic acid producing bacteria *Propionibacterium acidipropionici* immobilized in a fibrous bed bioreactor. In this fermentation, the fermentation pH is maintained at ~6.0, and the final propionate concentration reached ~100 g/L, which is ~2.5 times higher than that produced in a conventional propionic acid fermentation. However, the fermentation reaction may also utilize other propionic acid producing microorganisms, as the specific recitation of *Propionibacterium acidipropionici* is not meant to limit the scope of the invention.

In an alternative embodiment of the present invention, lactic acid fermentation has also been developed for lactic acid from glucose using the lactic acid producing filamentous fungus *Rhizopus oryzae*. The fermentation reaction may be carried out in a fed-batch extractive fermentation wherein the cells may be immobilized in a rotating fibrous bed bioreactor. The fermentation reaction is carried out wherein the pH is maintained at approximately pH 5. However, the fermentation reaction may also utilize other lactic acid producing microorganisms, as the specific recitation of *Rhizopus oryzae* is not meant to limit the scope of the invention.

In addition to the embodiments previously discussed, one skilled in the art will recognize that similar fermentation processes can be used to produce various carboxylic acids from different substrates using different microorganisms, including bacteria, yeasts, and filamentous fungi.

Following the fermentation process wherein fermentable carbohydrates are converted to organic acids by organic acid producing microorganisms, the organic acids are recovered from the fermentation broth and purified by extraction using an organic solvent, i.e. an extractant. In one specific embodiment of the present invention, the fermentation is preferably coupled with the extraction. This process, referred to as extractive-fermentation, allows for continuous production and recovery of the organic acids produced from the fermentation process in one continuous step. Extractive-fermentation significantly improves reactor productivity and final product concentration by reducing end-product inhibition, thus reducing downstream processing load and recovery costs.

In one embodiment, extraction of the organic acids in the fermentation broth may be preferably carried out with an extraction column. In one specific embodiment, the extraction column may be a packed extraction column wherein Alamine 336 is the extractant. The extraction column may alternatively comprise a Karr column. In an alternative embodiment, extraction of the organic acids in the fermentation broth may be carried out with a hollow-fiber membrane extractor.

In accordance with one embodiment of the present invention, the extractant is an amine solvent, and is preferably a water immiscible long-chain aliphatic amine solvent such as Alamine 336. Among the long-chain aliphatic amines, secondary (e.g., ditridecyl amine or Adogen 283) and tertiary amines (e.g., tricaprylyl amine or Alamine 336) are widely used because of their low solubility in water and high distribution coefficients for carboxylic acids. However, the organic acids produced during the fermentation process may also be extracted with other suitable extractants, as the specific recitation of the previously mentioned aliphatic amines is not meant to limit the scope of the invention.

Suitable extractants include those which are biocompatible, possess high extraction coefficients or $K_{eq}$ values for the product, are operable at a pH value close to optimal pH for fermentation, (usually ~5 or higher), or possess high distribution coefficients ($K_d$). Developing biocompatible extractants is difficult because solvents with high $K_{eq}$ values are usually toxic to cells. Additionally, suitable extractants should avoid phase separation problems. However, issues concerning phase separation can be overcome by using a membrane extractor to prevent direct contact between the extractant and the aqueous solution.

With regard to pH, efficient extraction requires an extractant with pH value below the $pK_a$ value of the organic acid. Most carboxylic acid fermentations have an optimal pH between 5 and 7. In an extractive-fermentation, there is no requirement that the pH of the fermentation broth be controlled with the addition of a base; rather, the pH of the fermentation broth can be kept at a pseudo-steady-state pH wherein the rate of organic acid production from the fermentation process is equal to the rate of organic acid removal by the extraction process. Thus, the removal of organic acid products by extraction reduces process wastes and production costs.

In one specific embodiment of the present invention, an extractive-fermentation has been developed for butyric acid production by butyric acid producing bacteria immobilized in a fibrous bed bioreactor. The butyric acid present in the fermentation broth can be recovered and purified by extraction using an aliphatic amine. By coupling the fermentation process with the extraction process, the resulting extractive-fermentation process can produce a higher butyrate concentration of >300 g/L at a higher productivity and purity than the non-coupled processes.

In an alternative embodiment of the present invention, an extractive-fermentation has also been developed for propionic acid production by *Propionibacterium acidipropionici* immobilized in a fibrous bed bioreactor. In this specific embodiment, the fermentation pH is maintained at ~4.8, and the final propionate concentration may reach ~170 g/L, which is 2.4 times higher than that which may be produced in a comparable fermentation reaction at pH 7.0.

As depicted in Table 1 set forth below, this specific extractive-fermentation may result in not only significantly higher reactor productivity, but also higher propionate yield and higher product purity than that of a batch fermentation. These effects may be attributed to a reduction in the production of acetate and succinate in the propionic acid fermentation. The increased product purity may also be attributed to the higher selectivity of amine extraction for propionic acid than for acetic and succinic acid.

TABLE 1

Comparisons of propionic acid production in extractive and conventional fermentations.

| | Batch Fermentation | | | Extractive Fermentation | |
|---|---|---|---|---|---|
| | pH 7.1 | pH 5.0 | pH 7.0* | pH 5.3 | pH 4.8* |
| Productivity (g/L · h) | 0.2 | 0.12 | 0.09/0.26* | 0.98 | 0.4/2.5* |
| Product Yield (g/g) | | | | | |
| Propionic acid | 0.31 | 0.54 | 0.4-0.65 | 0.66 | 0.78 |
| Acetic acid | 0.12 | 0.13 | 0.10 | 0.07 | 0.11 |
| Succinic acid | 0.10 | 0.09 | 0.09 | 0.02 | 0.01 |
| P/A Ratio | 2.58 | 4.15 | 4.0 | 9.8 | 7.1 |
| Product Purity | 58% | 71% | 69% | 88% | 88% |
| Final Propionate Concentration (g/L) | 12.5 | 18.5 | 71.7 | 75 | 170 |

*Fermentation with cells immobilized in a fibrous bed bioreactor (FBB). The higher productivity value is based on the FBB volume, whereas the lower value is based on the total liquid volume in the system.

In yet another embodiment of the present invention, an extractive-fermentation has been developed for lactic acid from glucose using the lactic acid producing microorganism *Rhizopus oryzae*. The extraction is carried out with Alamine 336 (30% in oleyl alcohol) followed by back extraction with 6 N NaOH in hollow-fiber membrane extractors. Lactic acid may be produced continuously at a stable rate, reaching a concentration of ~293 g/L in the stripping solution. The overall lactic acid yield is higher than 90% based on glucose consumption, with almost no byproduct produced in the fermentation process. Additionally, increasing the extractor capacity of the hollow fiber units, which is proportional to the total membrane surface area, may allow operation of the fermentation process at a higher pH, resulting in an increase in reactor productivity.

In yet still a further embodiment of the present invention, the organic acids present in the extractant may be separated from the extractant by stripping. The extractant can then be recycled back for use in the extraction process. The organic acids present in the extractant may be stripped by various reagents, including but not limited to: a base solution (e.g. NaOH), a strong acid solution (e.g. HCl), hot water, or steam. Stripping is most preferably accomplished with the use of a base because the base is energy efficient.

In accordance with one embodiment of the present invention, the organic acid extracted from the fermentation broth may be esterified following the extractive-fermentation. Esterification comprises reacting an organic acid with an alcohol in the presence of a catalyst. The catalyst used in the esterification reaction may include but is not limited to: sulfuric acid, a cation exchange resin (e.g. Amberlyst 15), or a biocatalyst. In one specific embodiment of the present invention, the catalyst is preferably an enzyme, and most preferably a lipase.

In one embodiment of the present invention, the organic acid in the extractant may be reacted directly with an alcohol in the presence of an enzyme, preferably a lipase, to form an ester that can be readily stripped with steam in a distillation column. The extractant may be regenerated and recycled for the extraction process, while the ester and unreacted alcohol may be separated in the distillation process. To carry out the esterification reaction in the extractant, an esterification process involving an immobilized lipase has been developed.

In one embodiment of the present invention, the esterification catalyst is preferably an enzyme, and most preferably a lipase. For esterification, various commercial lipases such as Novozyme 435 and non-commercial lipases produced either homologously or heterologously in microorganisms may be used. Extracellular lipases from *Candida lipolytica* may also be used for the esterification process. Among the three extracellular lipases found in *Candida lipolytica*, Lipase 2 is responsible for the major extracellular activity and has been widely used in hydrolysis, esterification and trans-esterification reactions. Mutants of *Candida lipolytica* sp. 99-125 can produce lipase at a high expression level of 6000 U/mL (1.1 g lipase/L) and with high productivity of 60 U/h/mL (11 mg/h/L). Mutants of *Candida lipolytica* sp. 99-125 can be obtained through a series of classic mutagenesis reactions.

In one embodiment of the present invention, the esterification reaction is carried out by immobilizing an enzyme on a support surface. More specifically, the esterification reaction is carried out by immobilizing the enzyme in a fibrous bed bioreactor. Immobilization of the enzyme involves the following steps: adsorption of the binding agent to a support surface, introduction of the enzyme to form aggregates with the binding agent, and cross linking the enzyme-binding agent aggregates coated on the support surface.

The immobilized enzyme reactor has a high productivity and good long-term stability for the esterification reaction to produce esters from acids and alcohols. In one specific embodiment of the present invention, a lipase is preferably immobilized on a support surface. In accordance with a further embodiment, the lipase is immobilized on a support surface comprising a fibrous matrix in a fibrous bed bioreactor. The esterification process with a lipase immobilized on a support surface can be operated continuously with a steady product stream for an extended period of months or longer without significant loss in its productivity. The support surface may comprise fibrous materials including synthetic fibers, such as polyester, glass fibers, and natural fibers, such as cotton and silk. In one specific embodiment wherein the lipase is immobilized on a support surface, the support surface is preferably a fibrous material comprising cotton.

Figure 2:
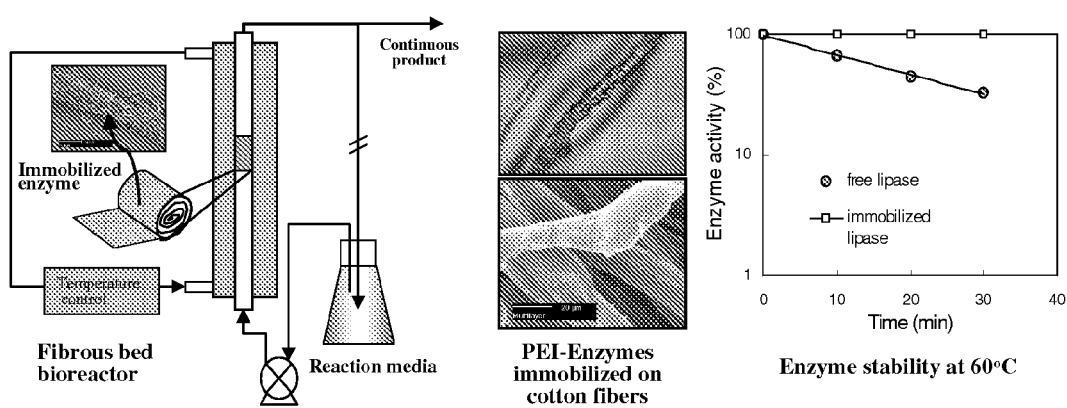
FIG. 2 illustrates the construction of a fibrous bed bioreactor (left) with enzyme immobilized on cotton fibers (center), and the thermal stability of immobilized lipase compared with free lipase at 60° C. (right).

In accordance with this specific embodiment, the binding agent may comprise but is not limited to alginate and charged polymers. In a preferred embodiment, the highly branched cationic polymer polyethyleneimine (PEI) is used. As depicted in FIG. 2, by preferably binding the enzyme to PEI as a binding agent, the enzyme may retain almost all of its activity (>90%) with an improved thermal stability (10 to 20-fold increase). Furthermore, as depicted in FIG. 2, immobilization of lipase on the fibrous support matrix is stable even at 60° C. as well as in the organic media used for the esterification reaction. Additionally, as depicted in FIG. 2, the immobilized enzyme was stable and retained almost all of its activity while the free enzyme lost more than 50% of its activity in 30 minutes.

In accordance with this specific embodiment, the cross-linking agent may comprise but is not limited to glutaraldehyde (GA). Once the enzyme is cross-linked with GA, the immobilized enzyme is stable and does not leach out from the support matrix. As previously discussed, FIG. 2 depicts the construction of an immobilized lipase reactor with an enzyme immobilized on the fibers.

In one specific embodiment of the present invention, the esterification of butyric acid and an alcohol, preferably ethanol or butanol, can be catalyzed by sulfuric acid, a cation exchange resin (e.g. Amberlyst 15), or a lipase enzyme. The esterification reaction is most preferably carried out wherein the catalyst is a lipase enzyme. Esterification with a lipase may be carried out under mild reaction conditions, i.e. ambient temperature and pressure.

Additionally, esterification with a lipase does not result in the production of byproducts, with the exception of water. With proper control on the water content in the reaction medium, a high product yield of greater than 90% with close to 100% conversion may be obtained. In one specific embodiment, wherein an ethyl butyrate ester is produced, a solvent other than ethanol, e.g. n-hexane is required for lipase catalysis.

Figure 3:
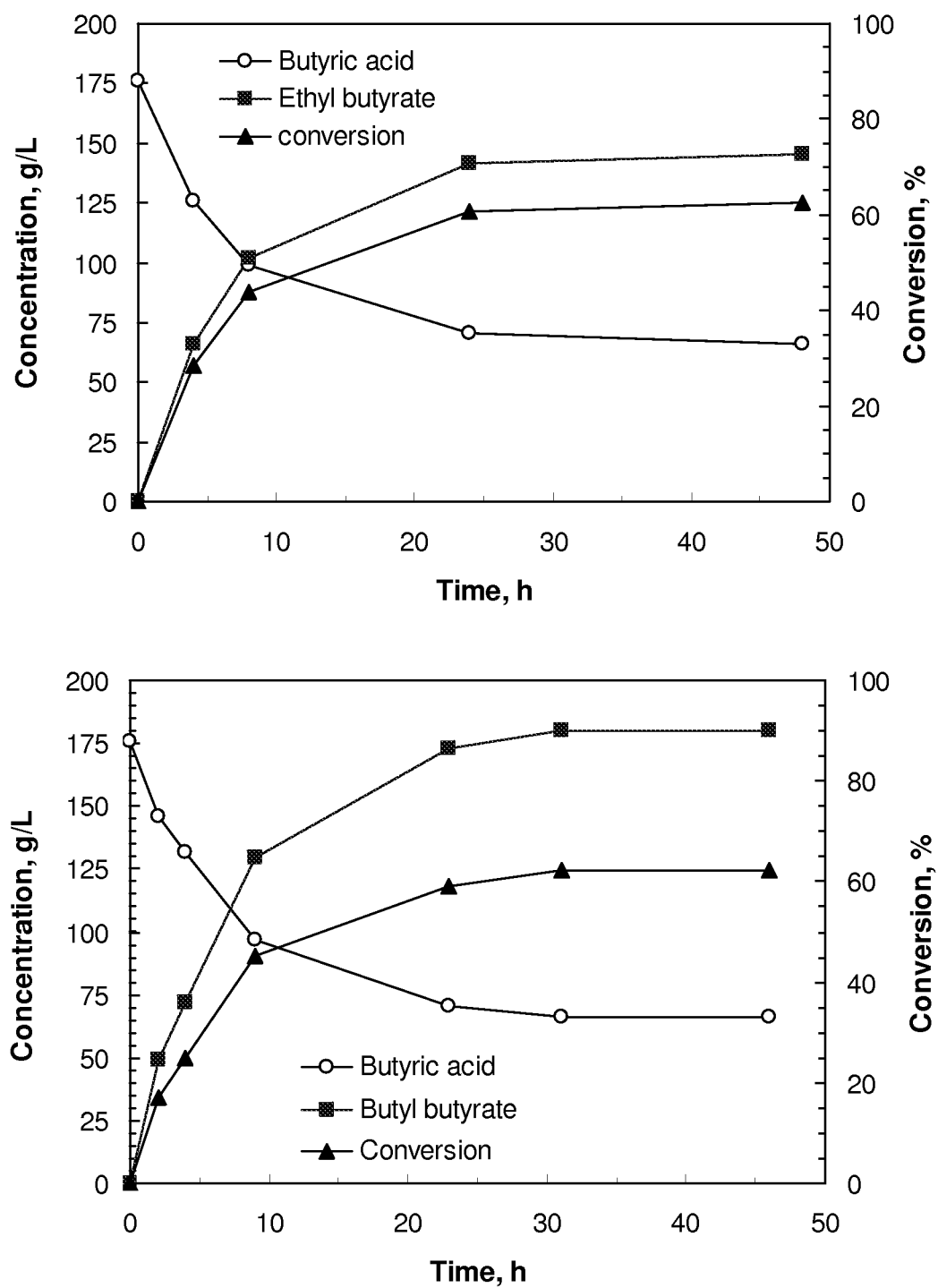
FIG. 3 is two graphs illustrating the kinetics of esterification of butyric acid with ethanol (top) or butanol (bottom) by immobilized lipase in a fibrous bed bioreactor.

According to embodiments of the present invention, enzymatic esterification of butyric acid by immobilized lipase in amine solvent and solvent free systems is feasible. In one specific embodiment, the organic acid present in the low molecular-weight tertiary amine, e.g., trialkyl amine, from the extractive fermentation process can be directly reacted with an alcohol to produce an ester. As depicted in FIG. 3, in one particular embodiment, about 65% conversion of butyric acid present in butanol to its ester may be achieved by immobilized lipase in a fibrous bed bioreactor wherein the butyric acid is not stripped from the extractant prior to esterification. In an alternative embodiment of the present invention, esterification of butyric acid in a solvent free system may occur when butanol is the alcohol substrate to produce butyl butyrate.

In accordance with one embodiment, as depicted in FIG. 3, a high ethyl butyrate concentration of 1.2 M (140 g/L) and butyl butyrate of 1.3 M (180 g/L) may be obtained with a conversion of 60% after 24 hours reaction in the amine solvent. In an alternative embodiment, a high butyl butyrate concentration of 1.9 M (272 g/L) may be obtained with a high conversion of 87% after 24 hours reaction in a solvent free system.

In one embodiment of the present invention wherein the esterification reaction takes place in the presence of an amine solvent, the reaction products, i.e. the ester and unreacted alcohol, are stripped from the extractant. More specifically, the ester and unreacted alcohol are stripped from the amine solvent with steam and are then separated in a distillation column. The amine solvent is thus regenerated and recycled for the extraction process as shown in FIG. 1.

Figure 4:
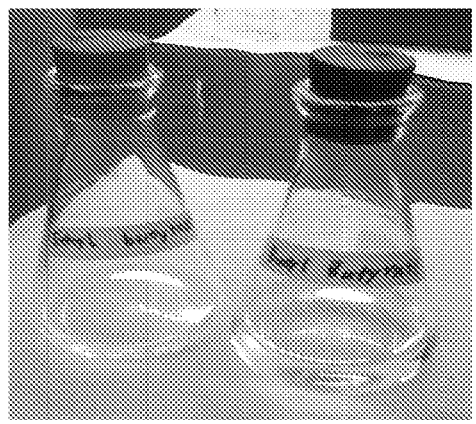
FIG. 4 is a photograph of 2 flasks containing the colorless ethyl butyrate (left) and butyl butyrate (right) esters produced from esterification and distillation.

In accordance with one specific embodiment of the present invention, as depicted in FIG. 4, colorless ethyl butyrate and butyl butyrate esters may be obtained from the reaction mixture by using distillation to separate the ester from the amine solvent and unreacted acid and alcohol.

Example 1

Materials and Methods

Enzymes and Reagents.

The lipase from *Candida* sp. 99-125 was produced in a fermentation process and then immobilized on cotton cloth, which was dried at room temperature and stored at 4° C. until use. The organic solvent consisted of Alamine 336 (straight chain tertiary amine containing $C_8$-$C_{10}$ alkyl groups, Henkel Corp. USA) and 2-octanol as the diluent. Unless otherwise noted, all chemicals, including lactic acid (85% w/w), ethyl lactate, isopropyl lactate and butyl lactate, used in this work were of analytical grade (Sigma, St. Louis, Mo.).

Esterification in Shake-Flasks.

Ester synthesis was carried out in 100 ml stoppered flasks with 10 ml of reaction mixture. The reaction was performed with 0.33 M lactic acid, 2.8 M ethanol, 0.33 M Alamine 336, 7 ml 2-octanol and 0.9 g immobilized lipase from *Candida* sp. 99-125, with a total volume of 10 ml. The mixture was incubated for 48 h in an orbital shaker at 30° C. and 150 rpm. Samples were taken at regular intervals and ethyl lactate and lactic acid were measured by using HPLC. All experiments were carried out in duplicate and mean values were reported.

Production of Ethyl Lactate in a Fibrous-Bed Bioreactor.

The lipase from *Candida* sp. 99-125 was produced in a fermentation process and was then immobilized on cotton cloth. Lipase was produced at a high expression level of 6000 U/mL (1.1 g lipase/L) and high productivity of 60 U/h/mL (11 mg/h/L). The cotton cloth was dried at room temperature and stored at 4° C. until use. Approximately 10.3 g of cotton cloth with immobilized lipase from *Candida* sp. 99-125 were packed in a column.

A reaction solution consisting of 0.33 M lactic acid, 2.8 M ethanol, 0.33 M Alamine 336 (straight chain tertiary amine containing $C_8$-$C_{10}$ alkyl groups, Henkel Corp. USA), and 35 ml 2-octanol, with a total volume of 50 ml, in an Erlenmeyer flask was recirculated through the packed column at 25° C. The flow rate was set at 5 mL/min. Samples were taken at regular intervals and the concentrations of ethyl lactate and lactic acid were analyzed by using HPLC. For long-term study to evaluate the operational stability, the reaction solution in the system was replaced with a fresh reaction solution every 24 h for 8 days. The reactor was then left idling in the room temperature until it was run again with a new batch of fresh reaction solution on day 21.

As depicted in FIG. 8, a study of the kinetics of lactic acid ester synthesis with lactic acid and various alcohols under the following reaction conditions was conducted: 0.9 g immobilized *Candida* sp. 99-125 lipase, 0.5 ml of 85% (w/w) lactic acid (30 g/l), 2.8 M alcohol, 1.5 ml of Alamine 336 and 2-octanol with a total volume of 10 ml at 30° C. and 150 rpm.

Example 2

Butyric Acid Production

An extractive-fermentation for butyric acid production from glucose by immobilized cells of *Clostridium tyrobutyricum* in a fibrous bed bioreactor was conducted. The extractant consisted of 10% (v/v) Alamine 336 in oleyl alcohol. The process was contained within a hollow-fiber membrane extractor to selectively remove butyric acid from the fermentation broth. The extractant was simultaneously regenerated by stripping with NaOH in a second membrane extractor. The fermentation pH was self-regulated by a balance between butyric acid production and removal of butyric acid by extraction, and was kept at ~pH 5.5 under the conditions studied. Compared to the conventional fermentation, the extractive fermentation gave a higher product concentration of >300 g/L and product purity of 91%. Extractive-fermentation also gave a higher reactor productivity of 7.37 g/L·h and butyric acid yield of 0.45 g/g.

For comparison, the same fermentation without on-line extraction to remove butyric acid resulted in a final butyric acid concentration of ~43.4 g/L, a butyric acid yield of 0.42 g/g, and a reactor productivity of 6.77 g/L·h when the pH was 6.0. When the pH was 5.5, the final butyric acid concentration was 20.4 g/L, the butyric acid yield was 0.38 g/g, and the reactor productivity was 5.11 g/L·h. The improved performance for the extractive fermentation can be attributed to reduced product inhibition by selectively removing butyric acid from the fermentation broth. The solvent was found to be toxic to free cells in suspension, but not harmful to cells immobilized in the fibrous bed bioreactor. The process was stable and gave consistent long-term performance for the entire 2-week period studied.

The butyric acid present in the extractant may be stripped by various methods, including stripping with a base solution (e.g. NaOH), a strong acid solution (e.g. HCl), or with hot water or steam. The butyric acid in the solvent also can be reacted directly with an alcohol to form an ester under the catalytic action of a lipase.

Example 3

Esterification

An integrated fermentation, extraction and esterification process, as depicted in FIG. 1, was employed to produce esters from alcohols and organic acids produced in fermentation. Butyric acid was first extracted into an amine solvent and was then reacted with butanol to form butyl butyrate ester. In this process, the stripping step was replaced with esterification, employing an alcohol and catalyst to catalyze the reaction between alcohol and organic acids present in the extractant. More specifically, in this process, the organic acids present in the extractant were directly reacted with alcohol to produce ester. As depicted in FIG. 3, more than 60% conversion of butyric acid to its ester with ethanol or butanol was achieved with the reaction in an organic solvent. The ester present in the amine solvent was separated by distillation or other methods and the amine solvent was then recycled back for use in the extraction process, as depicted in FIG. 1. A solvent free system was also employed when butanol is the alcohol substrate to produce butyl butyrate with a conversion of ~90%.

In the case of ethyl butyrate production, solvents other than ethanol (e.g. n-hexane) were needed for lipase catalysis. Esterification of butyric acid with butanol present in an organic solvent such as Alamine 336 was accomplished via the use of a lipase, preferably immobilized on a solid support.

As compared to free lipase, immobilized lipase offered many benefits, including enzyme reuse, easy separation of product from enzyme and the potential to run continuous processes via packed-bed reactors. Immobilized lipase had a shift toward a higher optimal temperature than that of free lipase. Also, the immobilized lipase esterification process was able to be operated continuously with a very steady product stream for an extended period of months or longer without significant loss in its productivity. FIG. 3 depicts the kinetics of esterification of butyric acid with ethanol (top) or butanol (bottom) by immobilized lipase in a fibrous bed bioreactor. As depicted in FIG. 3, a high ethyl butyrate concentration of 1.2 M (140 g/L) and butyl butyrate of 1.3 M (180 g/L) were obtained with a conversion of 60% after 24 h reaction in the amine solvent. Also, a high butyl butyrate concentration of 1.9 M (272 g/L) was obtained with a high conversion of 87% in a solvent-free system.

As depicted in FIG. 2, an immobilized lipase reactor was constructed with lipase immobilized on the fibers. The immobilized enzyme was stable at 60° C. and retained almost all of its activity while the free enzyme lost more than 50% of its activity in 30 minutes.

Immobilized lipase from *Candida* sp. 99-125 showed good catalytic ability for esterification of lactic acid. In general, increasing enzyme loading resulted in an increase in ester yield. The conversion rate for lactic acid to ethyl lactate ester increased from 18.5% at 0.45 g of lipase to 24% at 0.9 g lipase. Ethyl lactate was the only ester detected. Ethyl lactate was continuously produced in a plug-flow reactor for 21 days without significant decrease in the outlet product concentration, suggesting that the extractant was not toxic to lipase used in the esterification reaction. The results indicated that enzymatic esterification could be successfully carried out in an organic solvent.

Figure 5:
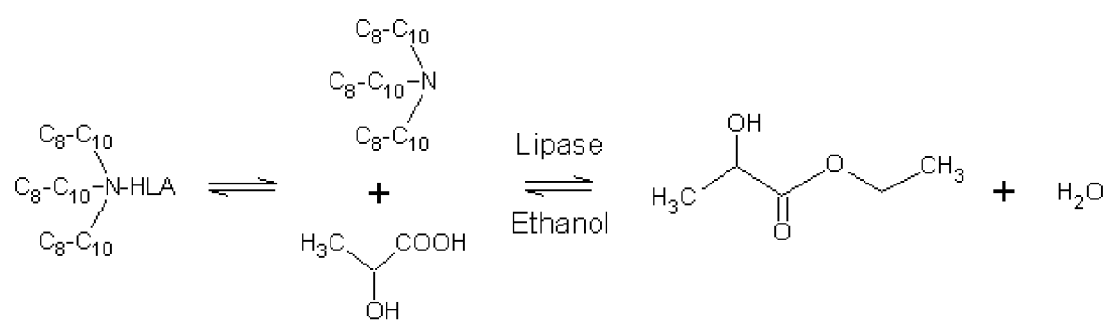
FIG. 5 shows the reaction mechanism of the esterification of lactic acid and ethanol with lipase in the extraction solvent consisting of Alamine 336 and 2-octanol.

FIG. 5 depicts the reaction mechanism of the esterification of lactic acid and ethanol with lipase in the extraction solvent consisting of Alamine 336 and 2-octanol. Novozyme 435 and immobilized lipase from *Candida* sp. 99-125 were used as catalysts for the esterification of lactic acid and ethanol. The preference of Novozyme 435 for the different enantiomers of lactic acid was previously investigated, finding that Novozyme 435 gives equal rate toward both enantiomers of lactic acid. Lipase from *Candida* sp. 99-125 was also found to catalyze the esterification of both enantiomers of lactic acid at almost equal rates. However, in the extraction solvent, lactic acid was found to exist as both an Alamine 336-lactic acid complex and as free lactic acid. Only free lactic acid was found to react with ethanol to produce ethyl lactate.

2-octanol was also found to react with lactic acid to form 2-octyl lactate. Esterification between 2-octanol and lactic acid was analyzed under various reaction systems. The conversion of 2-octanol to 2-octyl lactate was found to be 10.5% in 2-octanol without ethanol, whereas no 2-octyl lactate was detected in the reaction when 4M ethanol was present, suggesting that the lipase from *Candida* sp. 99-125 has a much lower activity towards secondary alcohol than primary alcohol.

Example 4

Production of Organic Acid Esters by Lipase in Extractant

The reaction kinetics of enzymatic esterification were studied with immobilized lipase from *Candida* sp. 99-125 in an extraction solvent used in extracting carboxylic acids from the fermentation broth. The effects of solvent concentration, molecular sieve for water removal, acid concentration, and molar ratio of alcohol to acid on the conversion of lactic acid to ethyl lactate were investigated. Ethyl lactate was continuously produced in a plug-flow reactor for 21 days without significant decrease in the outlet product concentration, suggesting that the extractant was not toxic to lipase used in the esterification reaction. The results indicated that enzymatic esterification could be successfully carried out in an organic solvent to produce organic acid esters from a fermentable carbon source and alcohols.

Effect of the Extractant.

Various organic solvents were investigated for their effects on the synthesis of ethyl lactate and the results are shown in Table 2 set forth below. The highest conversion (74%) was obtained in acetone, followed by the conversion of 63% and 33% in 2-octanol and 0.33 M Alamine 336 in 2-octanol, respectively. Cyclohexane and hexane with high log P value gave very low conversion. Cyclohexane and hexane, like other apolar solvents, were unable to completely dissolve lactic acid. Low lactic acid concentration in the solvent may have resulted in a low conversion. Undissolved lactic acid can deactivate lipase because of the high acidity of lactic acid. Another reason for the low conversion is that high water content [15% (w/w)] in lactic acid solution could produce saturation of high hydrophobic solvents, resulting in the shift of reaction equilibrium towards hydrolysis. High solubility of lactic acid in acetone and 2-octanol might contribute to the higher conversion to ester.

Lower conversion and initial rate were observed when Alamine 336 was added into 2-octanol. Fifty-one percent and 35% conversion was obtained in 0.15 M and 0.33 M Alamine, respectively, and 0.66 M Alamine 336 achieved only 6% conversion. Improvements in the initial rate and conversion were reported with the addition of trioctylamine into the hydrolysis reaction system of dynamic kinetic resolution of (R,S)-profen 2,2,2-trifluoroethyl thioesters using *Candida rugosa* lipase. The improvement was attributed to the ion-pair formation between the organo-soluble base and the product acid, which could prevent the acid inhibition and shift the reaction towards the products. Alamine 336 was found to react with lactic acid to form the ion-pair complex which resulted in a shift of the reaction towards the left-hand side (hydrolysis side), resulting in a lower ester conversion (see FIG. 5). Without using an organic solvent, the esterification reaction exhibited a low conversion of 5%, possibly due to the inactivation of lipase by lactic acid (acid inactivation) or excessive ethanol (dehydration).

TABLE 2

Effects of organic solvents on the production of ethyl lactate.

| Solvent | Log P | Reaction rate (µmol/h) | Conversion (%) |
| --- | --- | --- | --- |
| No solvent[a] | — | 1.2 | 5 |
| Acetonitrile | −0.33 | 10.9 | 16 |
| Acetone | −0.24 | 92.7 | 74 |
| n-Hexane | 3.5 | 2.7 | 4 |
| Cylcohexane | 3.2 | 3.4 | 8 |
| 2-octanol | 2.8 | 227.7 | 63 |
| 7.5% (v/v) Alamine 336 in 2-octanol | — | 229.5 | 51 |
| 15% (v/v) Alamine 336 in 2-octanol | — | 136.8 | 35 |
| 30% (v/v) Alamine 336 in 2-octanol | — | 10.4 | 6 |

Reaction conditions: 0.9 g immobilized Candida sp. 99-125 lipase, 0.5 ml of 85% (w/w) lactic acid (30 g/l), 1.6 ml of ethanol, 1.5 ml of Alamine 336 and 6.4 ml of organic solvents with a total volume of 10 ml at 30° C. and 150 rpm for 48 h.
[a]No solvent: ethanol was added instead of organic solvents.

Effect of Ethanol Concentration.

The effect of molar ratio of alcohol to acid on conversion of lactic acid to ester was studied. The conversion increased from 20% to 44% when the molar ratio of alcohol to acid increased from 0.5 to 16. Two reasons may explain the effect of molar ratio on conversion. First, excessive ethanol can drive the esterification reaction towards the products and result in a higher conversion. At the same time, excessive ethanol can also change solvent characteristics such as log P that can affect the activity of lipase. Excessive ethanol can also dissolve the water initially present in lactic acid (15%)

and water produced during esterification, which can also drive the reaction towards ester.

Effect of Water Absorbent.

Because hydrolysis is the reverse of esterification, the degree of hydration of solvent plays an important role in esterification conversion. Thus, the effect of water absorbent on the conversion was studied. Molecular sieve was added into the reaction system to remove water formed during esterification to drive the reaction towards products. Adding 1.0 g of molecular sieve to the reaction solution increased the conversion by about 5%.

Effects of Lactic Acid and Alamine 336 Concentrations.

As set forth below, Table 3 shows the effects of lactic acid and Alamine 336 concentrations on the initial rate and conversion of ethyl lactate. Conversion and initial rate decreased with increasing the Alamine 336 concentration when lactic acid concentration was low (0.15 M and 0.33 M). Low conversion and initial rate were obtained at different concentrations of lactic acid from 0.15 M to 1 M when a high Alamine 336 concentration of 0.66 M was used. A high lactic acid concentration of 1 M also gave a very low initial rate and conversion at different Alamine 336 concentrations. The optimum lactic acid concentrations at different Alamine 336 concentrations of 0.15 M, 0.33 M and 0.66 M was 0.33 M, 0.5 M and 0.5 M, respectively.

Three reasons may explain the effect of Alamine 336 concentrations. First, organic base of Alamine 336 can react with lactic acid to form the ion-pair complex, which reduces the amount of free lactic acid (reactive lactic acid) resulting in lower initial rate and conversion. Second, the addition of Alamine 336 can suppress the high acidity of lactic acid which deactivates the lipase activity. Finally, high concentrations of Alamine and lactic acid can change the characteristics of solvent, thus changing the solvation of the reaction components.

lactate esters. When butanol and 1-octanol were used as the acyl acceptor, the conversion was 54%, which is higher than the conversion obtained for ethyl lactate (37%). Secondary alcohols such as isopropanol gave a very low conversion of 7.7%. This result shows that *Candida* sp. 99-125 lipase is more active with primary and medium-chain alcohols.

Production of Organic Acid Esters.

The technology that couples extractive fermentation with enzymatic esterification can also be applied to ethyl butyrate and ethyl propionate production. FIG. 9 shows the synthesis of ethyl ester with ethanol and various short chain fatty acids. High conversions of 64% and 70% were obtained when butyric acid and propionic acid were used as the acyl donor, respectively. Acetic acid gave the lowest ester conversion of 22%. The conversion increased with an increase in the carbon chain length of the acid molecule.

This indicates that this lipase has a higher activity toward long-chain fatty acids. Water initially present in lactic acid solution can shift the reaction toward hydrolysis and resulted in low ethyl lactate conversion. The effect of butyric acid concentration on conversion is shown in FIG. 10. The initial rate and ethyl butyrate concentration increased with increasing the butyric acid concentration (up to 3 M), indicating that high butyric acid concentration would not inhibit or deactivate the enzyme.

From above examples, it is apparent that an integrated process with fermentation, extraction, and esterification units can produce various organic esters from organic acids and alcohols produced in fermentation. The organic acid is first extracted into an amine solvent and then reacted with alcohol to form the ester. In this process, the ester present in the amine solvent can be readily separated by steam stripping, and the amine solvent can then be recycled back for use in the extraction process. Further separation and purification of ester can be done by distillation, pervaporation, or nanofiltration, with

TABLE 3

Effects of lactic acid and Alamine 336 concentrations on ester conversion.

| Lactic acid concentration (g/L) | 7.5% (v/v) Alamine 336 | | 15% (v/v) Alamine 336 | | 30% (v/v) Alamine 336 | |
|---|---|---|---|---|---|---|
| | Initial rate (μmol/h/g) | Conversion (%) | Initial rate (μmol/h/g) | Conversion (%) | Initial rate (μmol/h/g) | Conversion (%) |
| 15 | 53.8 | 30.6 | 19.4 | 10.2 | 1.0 | 4.9 |
| 30 | 180 | 54 | 135 | 30.5 | 24.9 | 11.8 |
| 45 | 189 | 31 | 215 | 37.1 | 113 | 20.2 |
| 60 | 44.4 | 4.8 | 173 | 25.9 | 88.3 | 13.5 |
| 90 | 0.9 | 1.9 | 57.7 | 4.8 | 25.0 | 3 |

Reaction conditions: 0.9 g immobilized *Candida* sp. 99-125 lipase, 1:8 molar ratio of lactic acid to ethanol, 2-octanol with a total volume of 10 ml at 30° C. and 150 rpm.

Long-Term Production of Ethyl Lactate in a Fibrous Bed Bioreactor.

Figure 6:
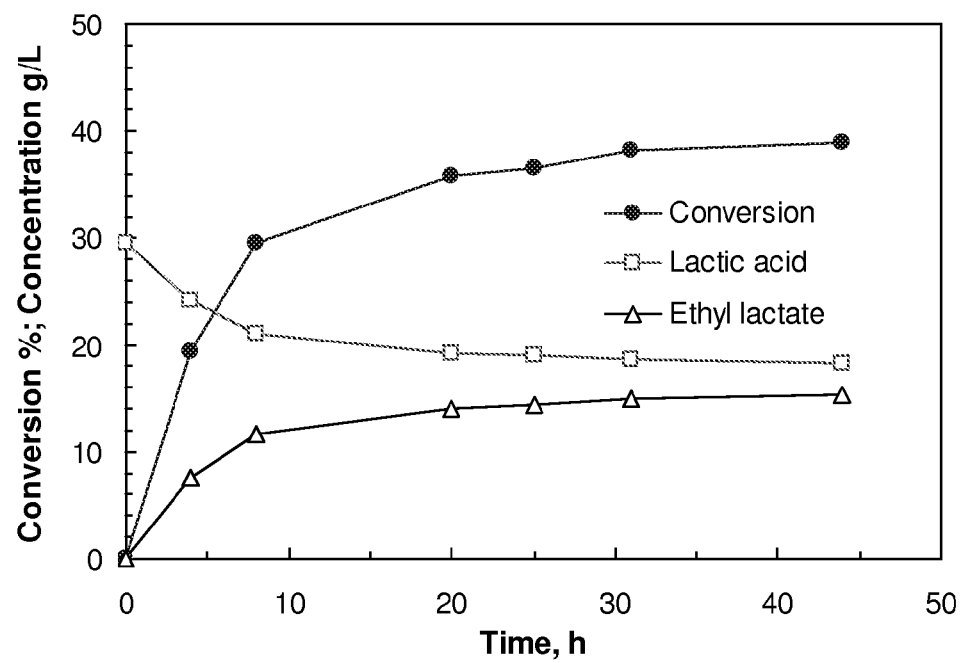
FIG. 6 is the time course of ethyl lactate synthesis in a recycle batch packed-bed immobilized lipase reactor under the following reaction conditions: 10.3 g immobilized lipase from *Candida* sp. 99-125, 2.5 ml of 85% (w/w) lactic acid (30 g/l), 8.0 ml of ethanol, 7.5 ml of Alamine 336 and 32 ml of 2-octanol with a total volume of 50 ml at 25° C. in the bioreactor.
Figure 7:
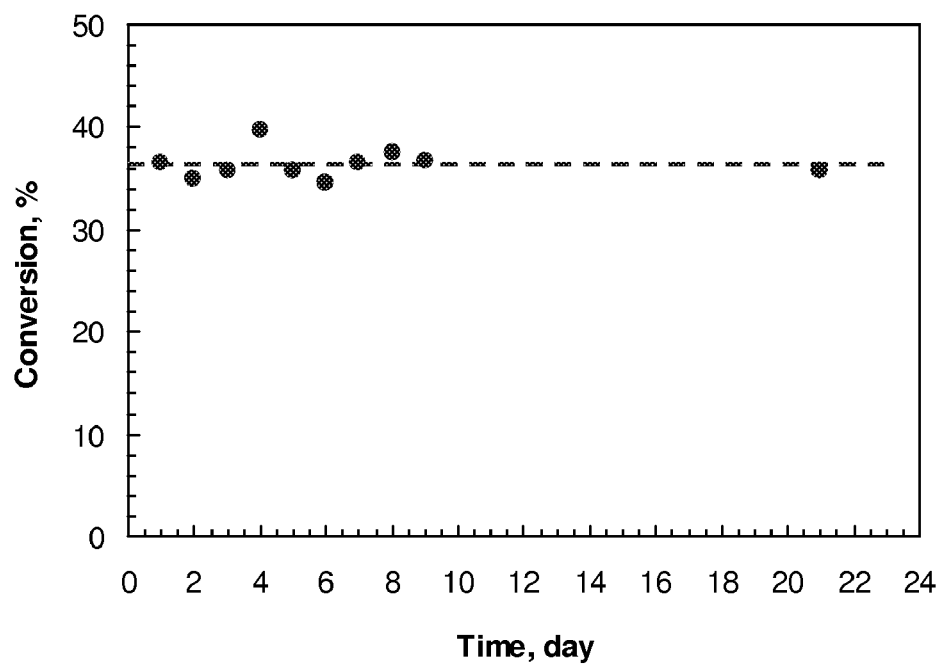
FIG. 7 shows the long-term operational stability of the immobilized lipase in a fibrous bed bioreactor at the repeated batch mode with the reaction conditions: 10.3 g immobilized lipase from *Candida* sp. 99-125, 2.5 ml of 85% (w/w) lactic acid (30 g/l), 8.0 ml of ethanol, 7.5 ml of Alamine 336 and 32 ml of 2-octanol with a total volume of 50 ml at 25° C. in the bioreactor for 24 h for each batch.

FIG. 6 shows the kinetics of esterification with immobilized lipase in a fibrous bed bioreactor under recycle batch conditions. The ethyl lactate conversion was 39% after 44 h. The operational stability of the enzyme was investigated for 21 days by operating the reactor in the repeated batch mode. As depicted in FIG. 7, the immobilized lipase was stable and there was no significant loss in enzyme activity as indicated by the stable conversion rate during the entire period of 21 days studied. Additionally, as depicted in FIG. 7, the immobilized lipase was stable and there was no significant loss in enzyme activity as indicated by the stable conversion rate during the entire period of 21 days studied.

Effect of Alcohol Chain Length on Esterification.

As depicted in FIG. 8, a study was conducted on the use of alcohols with different chain lengths to synthesize different the former being the preferred choice because it is commonly used in ethanol and butanol production plants.

Extractive fermentation to selectively separate the desirable product, such as butyric acid, in situ has the advantages of reducing product inhibition and increasing the fermentation rate and product yield. By selectively removing butyric acid from the fermentation broth continuously, the fermentation pathway may be shifted to produce more butyric acid and less of the byproducts (e.g., acetic acid), which also make product recovery and purification easier and less costly. Additionally, conducting enzymatic esterification in the extractant containing the fermentation produced butyric acid can dramatically reduce production costs for butyrate esters since there are no costly separation or purification steps involved in the process. Although the above examples substantially focus on butyric acid, the same technology described herein may also be applied to many other organic acids, i.e., acetic acid, propionic acid, lactic acid, citric acid, succinic acid, fumaric acid, itaconic acid, and long-chain fatty acids. The same technology may also be used to produce flavor ester compounds, such as amyl butyrate, and biodiesel from fusil oils and long-chain fatty acids present in food wastes.

With the fibrous bed bioreactor and extractive fermentation coupled with enzymatic esterification, high product yield, concentration, and reactor productivity can be achieved to reduce the product cost to a competitive level for commercial application, thus benefiting the bio-based industry by providing a viable avenue for better byproduct utilization and high-value products suitable for various markets. Additionally, the present invention may also economically convert fermentation produced butyric acid and ethanol to ethyl butyrate ester, which may be used as a biofuel.

It is noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of producing esters comprising:
   a) fermenting a fermentable carbon source in the presence of an organic acid producing microorganism to produce fermentation output comprising an organic acid;
   b) extracting the organic acid from the fermentation output into an extractant; and
   c) esterifying the organic acid in the extractant in the presence of a catalyst and alcohol to produce an organic ester, wherein the catalyst is selected from the group consisting of sulfuric acid, a cation exchange resin, and a lipase.

2. The method of claim 1, wherein the organic acid producing microorganism comprises at least one of *Clostridium tyrobutyricum, Clostridium butyricum, Clostridium beijerinckii, Clostridium populeti, Clostridium thermobutyricum, Rhizopus oryzae,* or *Propionibacterium aidipropionici.*

3. The method of claim 2, wherein the microorganism comprises engineered mutants of *Clostridium tyrobutyricum* ATCC 25755 obtained from inactivating the chromosomal ack gene encoding acetate kinase.

4. The method of claim 1, wherein the step of fermenting the fermentable carbon source in the presence of an organic acid producing microorganism to produce fermentation output comprising an organic acid is conducted at a pH from approximately 4 to 7.

5. The method of claim 1, wherein the fermentable carbon source is derived from biomass feedstock.

6. The method of claim 5, wherein the biomass feedstock comprises a carbohydrate source.

7. The method of claim 6, wherein the biomass feedstock comprises at least one of agricultural residues or processing wastes.

8. The method of claim 7, wherein the agricultural residues comprise corn stovers, corn cobs, and rice straw.

9. The method of claim 7, wherein the processing wastes comprise at least one of cheese whey or corn fibers.

10. The met hod of claim 1, wherein the step of fermenting the fermentable carbon source in the presence of an organic acid producing microorganism comprises the use of a fibrous bed bioreactor.

11. The method of claim 1, wherein the extractant is an amine solvent.

12. The method of claim 11, wherein the amine solvent is a long-chain aliphatic amine solvent.

13. The method of claim 1, wherein the lipase is produced from mutants of *Candida lipolytica* sp. 99-125.

14. The method of claim 1, wherein the lipase is immobilized on a support surface.

15. The method of claim 14, wherein the lipase is immobilized on a support surface comprising a fibrous matrix in a fibrous bed bioreactor.

16. The method of claim 1, wherein the organic ester is stripped from the extractant.

17. The method of claim 16, wherein the organic ester is stripped from the extractant with steam in a distillation column.

18. A method of producing esters comprising:

fermenting a fermentable carbon source in the presence of an organic acid producing microorganism to produce fermentation output comprising an organic acid;

extracting the organic acid into an organic solvent;

stripping the organic acid from the organic solvent; and esterifying the organic acid in the presence of a catalyst and alcohol to produce an organic ester.

19. The method of claim 18, wherein the step of stripping the organic acid from the organic solvent comprises the use of a base solution, a strong acid solution, hot water, or steam.

20. A method of producing esters comprising:

fermenting a carbohydrate source in the presence of engineered mutants of *Clostridium tyrobutyricum* ATCC 25755 obtained from inactivating the chromosomal ack gene encoding acetate kinase, to produce a fermentation output comprising butyric acid, extracting the butyric acid into an amine solvent; and esterifying the butyric acid in the presence of alcohol and a lipase immobilized on a fibrous bed bioreactor to produce a butyrate ester.

21. The method of claim 20, wherein the alcohol is at least one of butanol or ethanol.

22. The method of claim 15, wherein a binding agent is adsorbed on the support surface, wherein the binding agent is polyethylene glycol, wherein the lipase forms aggregates with the binding agent, wherein the aggregates are cross-linked with a cross-linking agent, and wherein the cross-linking agent is glutaraldehyde.

23. The method of claim 1, wherein the fermentation output is produced in a fermentation unit, the organic acid is extracted in an extraction unit, and the organic acid is esterified in an esterification unit, and wherein the fermenting, extracting, and esterifying are integrated such that the fermentation output flows from the fermentation unit to the extraction unit and the extractant flows from the extraction unit to the esterification unit.

* * * * *